US012345132B2

(12) United States Patent
Cao et al.

(10) Patent No.: US 12,345,132 B2
(45) Date of Patent: Jul. 1, 2025

(54) SIMULATION ANALYSIS METHOD FOR INJECTION VOLUME OF ALTERNATE DISPLACEMENT OF SHALE OIL BY CARBON DIOXIDE AND NITROGEN

(71) Applicants: SICHUAN INSTITUTE OF ENERGETICAL AND GEOLOGICAL SURVEY, Sichuan (CN); SICHUAN KEYUAN TESTING CENTER OF ENGINEERING TECHNOLOGY CO., LTD., Sichuan (CN)

(72) Inventors: Qian Cao, Sichuan (CN); Minghui Qi, Sichuan (CN); Yi Huang, Sichuan (CN); Yeyu Zhang, Sichuan (CN); Xu Peng, Sichuan (CN); Hongyu Du, Sichuan (CN); Hu Liu, Sichuan (CN)

(73) Assignees: SICHUAN INSTITUTE OF ENERGETICAL AND GEOLOGICAL SURVEY, Chengdu (CN); SICHUAN KEYUAN TESTING CENTER OF ENGINEERING TECHNOLOGY CO., LTD., Chengdu (CN)

( * ) Notice: Subject to any disclaimer, the term of this patent is extended or adjusted under 35 U.S.C. 154(b) by 892 days.

(21) Appl. No.: 17/480,363

(22) Filed: Sep. 21, 2021

(65) Prior Publication Data

US 2022/0003079 A1 Jan. 6, 2022

(51) Int. Cl.
*E21B 41/00* (2006.01)
*G01N 15/08* (2006.01)
(Continued)

(52) U.S. Cl.
CPC ............. *E21B 41/00* (2013.01); *G01N 15/08* (2013.01); *G01N 23/00* (2013.01); *G01N 33/24* (2013.01);
(Continued)

(58) Field of Classification Search
CPC ..... E21B 41/00; E21B 2200/20; G01N 15/08; G01N 23/00; G01N 33/24; G06F 30/20; G06F 2111/10; G06F 2113/08
See application file for complete search history.

(56) References Cited

U.S. PATENT DOCUMENTS

| | | | | |
|---|---|---|---|---|
| 2017/0030819 | A1* | 2/2017 | McCarty | E21B 43/26 |
| 2021/0079789 | A1* | 3/2021 | Zhi | G01V 3/32 |
| 2021/0123313 | A1* | 4/2021 | Westacott | G01N 33/0016 |

FOREIGN PATENT DOCUMENTS

| | | | | | |
|---|---|---|---|---|---|
| CN | 112304842 A | * | 2/2021 | | G01N 15/088 |
| CN | 112505084 A | * | 3/2021 | | G01N 1/28 |
| CN | 116539815 A | * | 8/2023 | | G01N 33/00 |

OTHER PUBLICATIONS

CN-112505084-A, English Translation (Year: 2021).*
CN-116539815-A, English Translation (Year: 2023).*
CN-112304842-A, English Translation (Year: 2021).*

* cited by examiner

*Primary Examiner* — Ryan D Walsh
(74) *Attorney, Agent, or Firm* — Porus IP LLC

(57) ABSTRACT

A simulation analysis method for an injection volume of alternate displacement of shale oil by carbon dioxide and nitrogen includes steps of simulating the alternate displacement of shale oil by carbon dioxide and nitrogen for multiple times through the core displacement simulation experiment, measuring the oil displacement efficiency change for every time, obtaining the porosity change in the entire displacement process through the porosity change before and after
(Continued)

alternate displacement, and building the injection volume adjustment expression of alternate displacement of shale oil by carbon dioxide and nitrogen as a reference of the injection volume of alternate displacement of shale oil by carbon dioxide and nitrogen, so that the total displacement efficiency in the actual mining process is improved, thus increasing the production rate of shale oil and reducing the usage amount of carbon dioxide. A simulation analysis device is used to carry out the simulation analysis method.

2 Claims, 2 Drawing Sheets

(51) Int. Cl.
*G01N 23/00* (2006.01)
*G01N 33/24* (2006.01)
*G06F 30/20* (2020.01)
*G06F 111/10* (2020.01)
*G06F 113/08* (2020.01)

(52) U.S. Cl.
CPC .......... *G06F 30/20* (2020.01); *E21B 2200/20* (2020.05); *G06F 2111/10* (2020.01); *G06F 2113/08* (2020.01)

SIMULATION ANALYSIS METHOD FOR INJECTION VOLUME OF ALTERNATE DISPLACEMENT OF SHALE OIL BY CARBON DIOXIDE AND NITROGEN

CROSS REFERENCE OF RELATED APPLICATION

The present invention claims priority under 35 U.S.C. 119(a-d) to CN 202011021630.9, filed Sep. 25, 2020.

BACKGROUND OF THE PRESENT INVENTION

Field of Invention

The present invention relates to the field of petroleum engineering technology, and more particularly to a simulation analysis method for an injection volume of alternate displacement of shale oil by carbon dioxide and nitrogen.

Description of Related Arts

Shale oil is the in-situ retained oil and gas resources contained in shale-dominated shale series of strata, which is not obvious in trap boundary and is unable to form natural industrial capacity. With the improvement of horizontal wells and staged fracturing technology and development capabilities, it has become the consensus of various countries that shale oil is the most likely energy source to replace oil and gas. Shale oil reservoir is an unconventional oil and gas reservoir, which has the characteristics of low permeability and low porosity, so traditional water flooding methods are difficult to be applied to shale oil reservoirs.

Due to the extraction capacity of $CO_2$ to crude oil and the strong adsorption of $CO_2$ in organic matter, $CO_2$ injection technology has become one of the effective means of developing shale oil reservoirs with potential and high efficiency. However, due to the greenhouse effect and gas source restrictions of carbon dioxide, in order to reduce the usage volume of carbon dioxide, exploring the displacement of shale oil by carbon dioxide and nitrogen has become a hot spot for shale oil development.

Due to the fact that there are still few studies on the alternate displacement of shale oil by carbon dioxide and nitrogen, the main research direction is still focused on the effectiveness of carbon dioxide and nitrogen in displacing shale oil. The research on the oil displacement efficiency, porosity change and carbon dioxide and nitrogen injection volume change of the alternate displacement of shale oil by carbon dioxide and nitrogen for many times is still blank.

SUMMARY OF THE PRESENT INVENTION

An object of the present invention is to overcome deficiencies mentioned above and provide an injection volume of alternate displacement of shale oil by carbon dioxide and nitrogen, which is adapted for simulating changes in oil displacement efficiency and porosity of oil shale under the mode of alternate displacement of shale oil by carbon dioxide and nitrogen, building the injection volume adjustment expression of alternate displacement of shale oil by carbon dioxide and nitrogen according to simulation results, and taking the injection volume adjustment expression as a reference of the injection volume of alternate displacement of shale oil by carbon dioxide and nitrogen during actual shale oil development.

To achieve the above object, the present invention provides technical solutions as follows.

A simulation analysis method for an injection volume of alternate displacement of shale oil by carbon dioxide and nitrogen, wherein the method comprises steps of:

(1) pretreating a shale core, performing a porosity test on the pretreated shale core, and measuring an initial porosity $p_0$ of the pretreated shale core;

(2) saturating the pretreated shale core with formation water after vacuumizing the pretreated shale core, pressurizing to a set pressure, displacing the formation water with manganese water, heating to a set temperature, saturating the shale core with crude oil at the set temperature and the set pressure, and measuring an NMR (nuclear magnetic resonance) T2 spectrum A in an initial state;

(3) performing temperature and pressure preservation, injecting carbon dioxide gases and nitrogen gases in sequence, measuring an NMR T2 spectrum B when an air pressure is balanced, and calculating a curve area difference between the NMR T2 spectrum B and the NMR T2 spectrum A at a same coordinate;

(4) repeating the step (3) till a curve area difference, between the NMR T2 spectrum N which is obtained at an $N^{th}$ alternate displacement, and the NMR T2 spectrum N−1 which is obtained at an $(N-1)^{th}$ alternate displacement at the same coordinate, is less than 0.5% of a curve area of the NMR T2 spectrum N which is obtained at the $N^{th}$ alternate displacement, and stopping repeating;

(5) vacuumizing a current shale core obtained by the step (4) again, and measuring a porosity p of the current shale core by helium method;

(6) based on a curve area difference, between the NMR T2 spectrum A in the initial state and the NMR T2 spectrum N which is obtained at the $N^{th}$ alternate displacement at the same coordinate, calculating a total oil displacement efficiency of alternate displacement of shale oil by carbon dioxide and nitrogen; based on curve area differences of NMR T2 spectrums, obtaining an expression of oil displacement efficiency change of alternate displacement of shale oil by carbon dioxide and nitrogen for multiple times; and based on the initial porosity $p_0$ and the porosity p, calculating a change rate of porosity of shale core before and after oil displacement; and (7) based on the expression of oil displacement efficiency change and the change rate of porosity of the shale core obtained by the step (6), obtaining an injection volume adjustment expression of alternate displacement of shale oil by carbon dioxide and nitrogen.

In the above technical solution, the NMR T2 spectrum during the oil displacement process is tested online by the NMR apparatus, so that the real-time NMR T2 spectrum of shale core under high temperature and high pressure is directly obtained, which is more in accordance with the actual situation during the oil displacement process. At the same time, in the above technical solution, the porosity of the shale core before and after the oil displacement thereof is measured, such that the porosity changes before and after the oil displacement are obtained. Because carbon dioxide is acidic, during the oil displacement process, the organic matter and clay material in the shale will be partially dissolved, and flow out of the shale core with at least one of carbon dioxide and shale oil. Accordingly, during the displacement process, with the displacement times increases, the porosity of the shale core is gradually changed. The injection volume of carbon dioxide and nitrogen has a significant effect on the displacement effect of shale oil. Therefore, it is very necessary to continuously adjust the injection volume of carbon dioxide and nitrogen during the displacement process. According to the porosity change and the oil displacement efficiency before and after displacement, the injection volume adjustment expression of alternate displacement of shale oil by carbon dioxide and nitrogen is obtained, which acts as a reference of the injection volume of alternate displacement of shale oil by carbon dioxide and nitrogen, so that the total oil displacement efficiency in the actual mining process is improved, thus increasing the production rate of shale oil and reducing the usage amount of carbon dioxide.

Preferably, in the step (6), the total oil displacement efficiency is equal to a ratio of the curve area difference between the NMR T2 spectrum A in the initial state and the NMR T2 spectrum N which is obtained at the $N^{th}$ alternate displacement at the same coordinate, to a curve area of the NMR T2 spectrum A in the initial state, which is expressed by a formula of $E_{total}=(S_0-S_N)/S_0\times100\%$, wherein $E_{total}$ is the total oil displacement efficiency, $S_0$ is the curve area of the NMR T2 spectrum A in the initial state, $S_N$ is the curve area of the NMR T2 spectrum N at the $N^{th}$ alternate displacement.

In the technical solution mentioned above, the oil displacement efficiency of shale oil is calculated by the curve area difference of NMR T2 spectrums, which is better in accuracy and is able to better reflect the real-time oil displacement efficiency for alternate displacement of shale oil by carbon dioxide and nitrogen for multiple times compared with the traditional weight method.

Preferably, in the step (6), obtaining the expression of oil displacement efficiency change of alternate displacement of shale oil by carbon dioxide and nitrogen for multiple times comprises:

(6A) based on an NMR T2 spectrum M which is obtained at the $M^{th}$ alternate displacement, and an NMR T2 spectrum M−1 which is obtained at the $(M-1)^{th}$ alternate displacement, wherein M is integer greater than 1, obtaining an area difference between NMR T2 spectrums of alternate displacement of shale oil by carbon dioxide and nitrogen for two adjacent times;

(6B) based on the area difference obtained by the step (6A), obtaining an oil displacement efficiency of alternate displacement of shale oil by carbon dioxide and nitrogen for one of the two adjacent times; and (6C) based on the oil displacement efficiency obtained by the step (6B), fitting a relational expression between the oil displacement efficiency and an alternate displacement time of alternate displacement of shale oil by carbon dioxide and nitrogen for multiple times with polynomials, thereby obtaining the expression of oil displacement efficiency change of alternate displacement of shale oil by carbon dioxide and nitrogen for multiple times.

Preferably, in the step (6), the change rate of porosity is a ratio of a difference between the initial porosity $p_0$ and the porosity p, and the initial porosity $p_0$, which is expressed by a formula of $P_{change\ rate}=(p_0-p)/p_0\times100\%$.

Preferably, in the step (7), the injection volume adjustment expression of alternate displacement of shale oil by carbon dioxide and nitrogen is obtained by a method comprising:

(7A) obtaining a relational expression between the change rate of porosity and the alternate displacement time of alternate displacement of shale oil by carbon dioxide and nitrogen for multiple times by substituting the change rate of porosity into the expression of oil displacement efficiency change of alternate displacement of shale oil by carbon dioxide and nitrogen for multiple times;

(7B) building calculation formulas between an injection volume of alternate displacement of shale oil by carbon dioxide and nitrogen for every time and a porosity of the shale core at this time; and (7C) substituting the calculation formulas obtained by the step (7B) into the relational expression obtained by the step (7A), thereby obtaining the injection volume adjustment expression of alternate displacement of shale oil by carbon dioxide and nitrogen.

Preferably, in the step (7B), the calculation formulas are $V_{total}=V_{mCO2}+V_{mN2}$, $V_{mCO2}=p_m\times V_{shale\ core}\times0.3$, and $V_{mN2}=p_m\times V_{shale\ core}\times0.2$, wherein $V_{total}$ is a total injection volume of alternate displacement of shale oil by carbon dioxide and nitrogen for every time, m is the $m^{th}$ alternate displacement time and meets a condition of $1\leq m\leq N$, $V_{mCO2}$ is an injection volume of carbon dioxide of alternate displacement of shale oil by carbon dioxide and nitrogen for the $m^{th}$ time, $V_{mN2}$ is an injection volume of nitrogen of alternate displacement of shale oil by carbon dioxide and nitrogen for the $m^{th}$ time, $p_m$ is a porosity of the shale core of alternate displacement of shale oil by carbon dioxide and nitrogen for the $m^{th}$ time, $V_{shale\ core}$ is a volume of the shale core.

Preferably, in the step (3), a volume of the injected carbon dioxide gases is 0.3 times a void volume of the shale core for the first time, a volume of the injected nitrogen gases is 0.2 times the void volume of the shale core for the first time, an injection pressure of carbon dioxide and nitrogen is in a range of 20 to 30 MPa.

Preferably, pretreating the shale core comprises cleaning and drying the shale core for cleaning mobile phases such as oil phase, water phase and gas phase in the shale core, so as to improve the accuracy of test data.

Preferably, in the step (2), a concentration of divalent manganese ions in the manganese water is in a range of 0.5 to 2 g/L, the manganese water is prepared by using formation water as a solvent. The shale core saturated by formation water which is prepared with divalent manganese ions eliminates the nuclear magnetic signal of hydrogen in the formation water in the core sample by the divalent manganese ions, so that the spectrum determined by nuclear magnetic resonance is the spectrum of crude oil.

Also, the present invention provides a simulation analysis device for an injection volume of alternate displacement of shale oil by carbon dioxide and nitrogen, which comprises a core package apparatus, a nuclear magnetic resonance apparatus, a control apparatus, a confining pressure apparatus, a gas supply pipeline, a gas discharging pipeline, a nitrogen cylinder, a carbon dioxide cylinder, a helium cylinder and a vacuum pump, wherein the core package apparatus comprises an elastic rubber tube, a first head and a second head both of which are respectively located at two ends of the elastic rubber tube; the first head has a gas inlet which is communicated with the gas supply pipeline; the second head has a gas pumping port which is communicated with the vacuum pump, and an oil outlet which is communicated with the gas discharging pipeline; the nitrogen cylinder, the carbon dioxide cylinder and the helium cylinder are communicated with the gas inlet of the core package apparatus through a first sub-pipeline, a second sub-pipeline and a first branch pipeline of the gas supply pipeline, respectively; a nitrogen control valve, a carbon dioxide control valve and a helium control valve are provided on the first sub-pipeline, the second sub-pipeline and the first branch pipeline of the gas supply pipeline for controlling opening and closing of the nitrogen cylinder, the carbon dioxide cylinder and the helium cylinder, respectively; a pressure monitoring apparatus and a temperature monitoring apparatus are provided on the confining pressure apparatus; the confining pressure apparatus comprises an annular confining pressure housing located at an outer side of the core package apparatus, wherein the annular confining pressure housing and an outer side wall of the core package apparatus form a confining pressure chamber, the core package apparatus is communicated with the confining pressure chamber through the gas inlet, the gas pumping port and the oil outlet; a flow monitoring apparatus and another pressure monitoring apparatus are installed at each of the gas inlet, the gas pumping port and the oil outlet of the core package apparatus; the nuclear magnetic resonance apparatus comprises a probe for measuring and obtaining NMR spectrums of the shale core and a computer; the control apparatus comprises the nitrogen control valve, the carbon dioxide control valve, the helium control valve, multiple flow monitoring apparatuses, multiple pressure monitoring apparatuses and multiple temperature monitoring apparatuses for controlling corresponding elements, respectively.

The aforementioned simulation analysis device is suitable for not only the method for oil displacement effectiveness disclosed by the present invention, and but also other core simulation experiments.

Compared with prior arts, the present invention has some beneficial effects as follows.

In the simulation analysis method for an injection volume of alternate displacement of shale oil by carbon dioxide and nitrogen mentioned above, the NMR T2 spectrum during the oil displacement process is tested online by the NMR apparatus, so that the real-time NMR T2 spectrum of shale core under high temperature and high pressure is directly obtained, which is more in accordance with the actual situation during the oil displacement process. At the same time, in the above technical solution, the porosity of the shale core before and after the oil displacement thereof is measured, such that the porosity changes before and after the oil displacement are obtained. Because carbon dioxide is acidic, during the oil displacement process, the organic matter and clay material in the shale will be partially dissolved, and flow out of the shale core with at least one of carbon dioxide and shale oil. Accordingly, during the displacement process, with the displacement times increases, the porosity of the shale core is gradually changed. The injection volume of carbon dioxide and nitrogen has a significant effect on the displacement effect of shale oil. Therefore, it is very necessary to continuously adjust the injection volume of carbon dioxide and nitrogen during the displacement process. According to the porosity change and the oil displacement efficiency before and after displacement, the injection volume adjustment expression of alternate displacement of shale oil by carbon dioxide and nitrogen is obtained, which acts as a reference of the injection volume of alternate displacement of shale oil by carbon dioxide and nitrogen, so that the total oil displacement efficiency in the actual mining process is improved, thus increasing the production rate of shale oil and reducing the usage amount of carbon dioxide.

Figure 1:
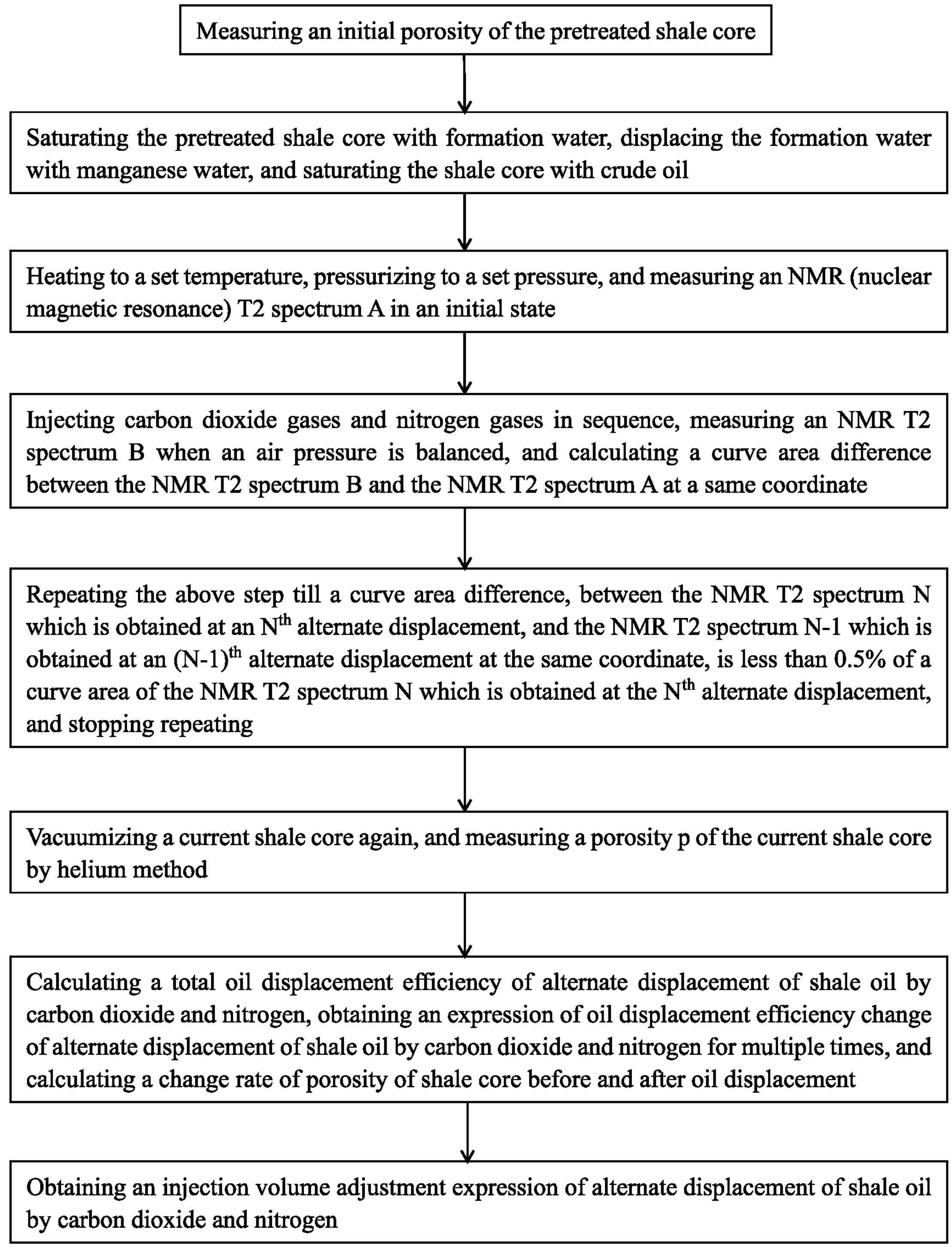
FIG. 1 is a flow chart of a simulation analysis method for an injection volume of alternate displacement of shale oil by carbon dioxide and nitrogen provided by the present invention.

In the drawings, 1: core package apparatus; 2: nuclear magnetic resonance apparatus; 3: confining pressure apparatus; 4: gas supply pipeline; 5: gas discharging pipeline; 6: nitrogen cylinder; 7: carbon dioxide cylinder; 8: helium cylinder; 9: vacuum pump; 10: preheating and pressure regulating chamber; 101: first head; 102: second head; 104: elastic rubber tube; 301: annular confining pressure housing; 302: confining pressure chamber; 1001: first sub-pipeline; 1002: second sub-pipeline; 1011: gas inlet; 1021: gas pumping port; 1022: oil outlet; 4000: main pipeline; 4001: first branch pipeline; 4002: second branch pipeline; 10031: gas outlet; 40021: helium control valve; 40022: nitrogen control valve; 40023: carbon dioxide control valve.

DETAILED DESCRIPTION OF THE PREFERRED EMBODIMENT

The present invention will be further explained in combination with experimental cases and specific embodiments. However, it should not be understood that the scope of the above-mentioned subject of the present invention is limited to the following embodiments, and all technologies implemented based on the content of the present invention belong to the protective scope of the present invention.

In the prior art, the effect of using water displacement to extract shale oil is not good. In order to improve the oil displacement efficiency of shale oil, a gas displacement method for shale oil has been developed, in which the displacement of shale oil by carbon dioxide is currently the main displacement method for shale oil production. However, due to the influence of carbon dioxide gas source and environmental requirements, it is necessary to reduce the volume of carbon dioxide used in the process of carbon dioxide displacement. Accordingly, Patent CN 108397171 A proposes a method for alternate displacement of shale oil by carbon dioxide and nitrogen. However, in the process of multiple alternate displacements, with the displacement of crude oil and the dissolution effect of carbon dioxide on the organic matter or clay in the rock formation, the porosity of the rock formation will gradually change. If the injection volume of carbon dioxide and nitrogen is not changed, it is difficult to achieve a better displacement effect. There is a lack of research on the variation of injection volume in the existing technology. Therefore, the present invention provides a simulation analysis method for an injection volume of alternate displacement of shale oil by carbon dioxide and nitrogen, which comprises simulating the alternate displacement of shale oil by carbon dioxide and nitrogen for multiple times through the core displacement simulation experiment, measuring the oil displacement efficiency change for every time, obtaining the porosity change in the entire displacement process through the porosity change before and after alternate displacement, and building the injection volume adjustment expression of alternate displacement of shale oil by carbon dioxide and nitrogen as a reference of the injection volume of alternate displacement of shale oil by carbon dioxide and nitrogen.

In a simulation analysis method for an injection volume of alternate displacement of shale oil by carbon dioxide and nitrogen provided by the present invention, a core displacement simulation experiment is carried out by a device as follows.

Figure 2:
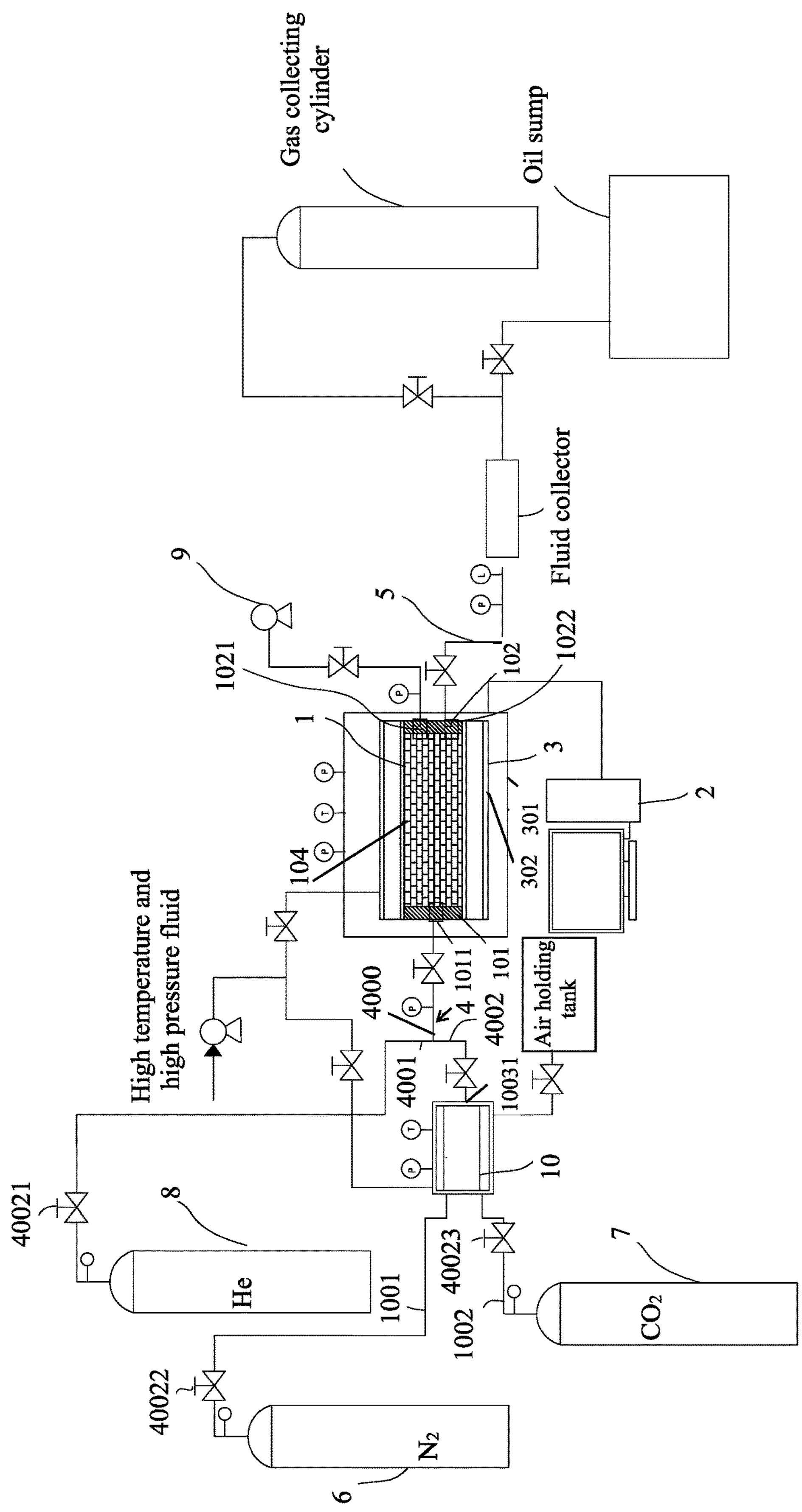
FIG. 2 is a structurally schematic view of a device used in the simulation analysis method for an injection volume of alternate displacement of shale oil by carbon dioxide and nitrogen provided by the present invention.

Referring to FIG. 2, the device comprises a core package apparatus 1, a nuclear magnetic resonance apparatus 2, a control apparatus, a confining pressure apparatus 3, a gas supply pipeline 4, a gas discharging pipeline 5, a nitrogen cylinder 6, a carbon dioxide cylinder 7, a helium cylinder 8 and a vacuum pump 9, wherein the core package apparatus 1 comprises an elastic rubber tube 104, a first head 101 and a second head 102 both of which are respectively located at two ends of the elastic rubber tube 104; the first head 101 has a gas inlet 1011 which is communicated with the gas supply pipeline 4; the second head 102 has a gas pumping port 1021 which is communicated with the vacuum pump 9, and an oil outlet 1022 which is communicated with the gas discharging pipeline 5; the nitrogen cylinder 6, the carbon dioxide cylinder 7 and the helium cylinder 8 are communicated with the gas inlet 1011 of the core package apparatus 1 through a first sub-pipeline 1001, a second sub-pipeline 1002 and a first branch pipeline 4001 of the gas supply pipeline 4, respectively; a nitrogen control valve 40022, a carbon dioxide control valve 40023 and a helium control valve 40021 are provided on the first sub-pipeline 1001, the second sub-pipeline 1002 and the first branch pipeline 4001 of the gas supply pipeline 4 for controlling opening and closing of the nitrogen cylinder 6, the carbon dioxide cylinder 7 and the helium cylinder 8, respectively; a pressure monitoring apparatus (abbreviated as P) and a temperature monitoring apparatus (abbreviated as T) are provided on the confining pressure apparatus 3; the confining pressure apparatus 3 comprises an annular confining pressure housing 301 located at an outer side of the core package apparatus 1, wherein the annular confining pressure housing 301 and an outer side wall of the core package apparatus 1 form a confining pressure chamber 302, the core package apparatus 1 is communicated with the confining pressure chamber 302 through the gas inlet 1011, the gas pumping port 1021 and the oil outlet 1022 for injecting fluid to make a confining pressure of the core package apparatus 1 reach a set value, the injected fluid is high-temperature fluid for heating shale core to make the shale core reach a set temperature, so as to carry out shale oil displacement under high temperature and high pressure; the nuclear magnetic resonance apparatus 2 is configured to measure and obtain a nuclear magnetic resonance T2 spectrum of the shale core which is processed by a computer and presented; the control apparatus comprises the nitrogen control valve 40022, the carbon dioxide control valve 40023, the helium control valve 40021, multiple flow monitoring apparatuses, multiple pressure monitoring apparatuses and multiple temperature monitoring apparatuses for controlling corresponding elements, respectively.

The device further comprises a preheating and pressure regulating chamber 10 for preheating and regulating the pressure of nitrogen gases and carbon dioxide gases, wherein the preheating and pressure regulating chamber 10 is provided on a part of the gas supply pipeline 4 which connects the nitrogen cylinder 6 with the carbon dioxide cylinder 7. The gas supply pipeline 4 comprises a main pipeline 4000, a first branch pipeline 4001, a second branch pipeline 4002, a first sub-pipeline 1001 and a second sub-pipeline 1002, wherein one end of the main pipeline 4000 is connected with the gas inlet 1011 of the core package apparatus 1, another end of the main pipeline 4000 is connected with the first branch pipeline 4001 and the second branch pipeline 4002, respectively; one end of the first branch pipeline 4001 away from the main pipeline 4000 is connected with the helium cylinder 8, one end of the second branch pipeline 4002 away from the main pipeline 4000 is connected with a gas outlet 10031 of the preheating and pressure regulating chamber 10; one end of the first sub-pipeline 1001 is connected with the nitrogen cylinder 6, another end of the first-pipeline is connected with the preheating and pressure regulating chamber 10; one end of the second sub-pipeline 1002 is connected with the carbon dioxide cylinder 7, another end of the second sub-pipeline 1002 is connected with the preheating and pressure regulating chamber 10. A check valve, the helium control valve 40021, another check valve, the nitrogen control valve 40022 and the carbon dioxide control valve 40023 are located on the main pipeline 4000, the first branch pipeline 4001, the second branch pipeline 4002, the first sub-pipeline 1001 and the second sub-pipeline 1002 for controlling gas flow and gas reflux thereof, respectively.

In order to solve technical problems mentioned above, the present invention provides a simulation analysis method for an injection volume of alternate displacement of shale oil by carbon dioxide and nitrogen, as shown in FIG. 1, wherein the method comprises steps of:

(1) pretreating a shale core, putting the pretreated shale core into the core package apparatus 1, wherein two ends of the shale core are tightly pressed to the first head 101 and the second head 102 of the core package apparatus 1, the elastic rubber tube 104 of the core package apparatus 1 is tightly pressed to an external surface of the shale core, closing the vacuum pump 9 after vacuumizing the shale core through the vacuum pump 9 for the first time, introducing helium gases into the core package apparatus 1 by opening the helium control valve 40021, and measuring an initial porosity $p_0$ of the shale core by helium method, wherein the external surface of the shale core are smooth;

(2) closing the vacuum pump 9 after vacuumizing the shale core through the vacuum pump 9 for the second time, opening the fluid inlet and a fluid outlet of the confining pressure apparatus 3, saturating the shale core with formation water by injecting the formation water at a set temperature into the confining pressure chamber 302, pressurizing to a set pressure, saturating the shale core with manganese water by displacing the formation water with the manganese water, saturating the shale core with crude oil by injecting the crude oil into the confining pressure chamber 302, adjusting an amount of fluid from the fluid outlet, heating and pressurizing the core package apparatus 1 with the confining pressure apparatus 3 to the set temperature and the set pressure, and measuring an NMR (nuclear magnetic resonance) T2 spectrum A in an initial state;

(3) performing temperature and pressure preservation, opening the carbon dioxide control valve 40023, injecting carbon dioxide gases into the core package apparatus 1, wherein a volume of the injected carbon dioxide gases is 0.3 times a void volume of the shale core; opening the nitrogen control valve 40022, injecting nitrogen gases into the core package apparatus 1, wherein a volume of the injected nitrogen gases is 0.2 times the void volume of the shale core; measuring an NMR T2 spectrum B when an air pressure at two ends of the core package apparatus 1 is balanced, and calculating a curve area difference between the NMR T2 spectrum B and the NMR T2 spectrum A at a same coordinate;

(4) repeating the step (3) till a curve area difference, between the NMR T2 spectrum N which is obtained at an $N^{th}$ alternate displacement, and the NMR T2 spectrum N−1 which is obtained at an $(N-1)^{th}$ alternate displacement at the same coordinate, is less than 0.5% of a curve area of the NMR T2 spectrum N which is obtained at the $N^{th}$ alternate displacement, and stopping repeating;

(5) closing the vacuum pump 9 after vacuumizing the shale core through the vacuum pump 9 for the third time, and measuring a porosity p of the shale core by the helium method;

(6) based on a curve area difference, between the NMR T2 spectrum A in the initial state and the NMR T2 spectrum N which is obtained at the $N^{th}$ alternate displacement at the same coordinate, calculating a total oil displacement efficiency of alternate displacement of shale oil by carbon dioxide and nitrogen; based on curve area differences of NMR T2 spectrums, obtaining an expression of oil displacement efficiency change of alternate displacement of shale oil by carbon dioxide and nitrogen for multiple times; and based on the initial porosity $p_0$ and the porosity p, calculating a change rate of porosity of the shale core before and after oil displacement; and (7) based on the expression of oil displacement efficiency change and the change rate of porosity of the shale core obtained by the step (6), obtaining an injection volume adjustment expression of alternate displacement of shale oil by carbon dioxide and nitrogen.

Preferably, in the step (6), the total oil displacement efficiency is equal to a ratio of the curve area difference between the NMR T2 spectrum A in the initial state and the NMR T2 spectrum N which is obtained at the $N^{th}$ alternate displacement at the same coordinate, to a curve area of the NMR T2 spectrum A in the initial state, which is expressed by a formula of $E_{total}=(S_0-S_N)/S_0\times100\%$, wherein $E_{total}$ is the total oil displacement efficiency, $S_0$ is the curve area of the NMR T2 spectrum A in the initial state, $S_N$ is the curve area of the NMR T2 spectrum N at the $N^{th}$ alternate displacement.

In the technical solution mentioned above, the oil displacement efficiency of shale oil is calculated by the curve area difference of NMR T2 spectrums, which is better in accuracy and is able to better reflect the real-time oil displacement efficiency for alternate displacement of shale oil by carbon dioxide and nitrogen for multiple times compared with the traditional weight method.

It should be noted that the curve area difference is that taking the NMR T2 spectrum A in the initial state and the NMR T2 spectrum B which is measured at the first alternate displacement of shale oil by carbon dioxide and nitrogen as an example, intersections of the NMR T2 spectrum A and the NMR T2 spectrum B appear at the same coordinate; the intersections, the NMR T2 spectrum A and the NMR T2 spectrum B form at least one closed region, an area of the at least one closed region is calculated to obtain the curve area difference. Moreover, the curve area difference described in the present invention is the area which is covered by non-overlapping regions enclosed by two NMR T2 spectrums at the same coordinate.

Preferably, pretreating a shale core comprises cleaning and drying the shale core for cleaning mobile phases such as oil phase, water phase and gas phase in the shale core, so as to improve the accuracy of test data. Specifically, pretreating a shale core comprises cutting a sample into the shale core required according to a size of the core package apparatus 1, cleaning fluid-state oil and water in the shale core, and drying, thereby obtaining a pretreated shale core.

Preferably, in the step (2), a concentration of divalent manganese ions in the manganese water is in a range of 0.5 to 2 g/L, the manganese water is prepared by using formation water as a solvent, and more preferably, manganese chloride is used to prepare the manganese water.

Preferably, the initial porosity $p_0$ and the porosity p of the shale core are also able to be measured by weight method.

Preferably, the set temperature and the set pressure are determined by an actual formation temperature and an actual formation pressure collected by the shale core, and are also able to be determined by experimental requirements.

Preferably, in the step (6), obtaining the expression of oil displacement efficiency change of alternate displacement of shale oil by carbon dioxide and nitrogen for multiple times comprises:

(6A) based on an NMR T2 spectrum M which is obtained at the $M^{th}$ alternate displacement, and an NMR T2 spectrum M−1 which is obtained at the $(M-1)^{th}$ alternate displacement, wherein M is integer greater than 1, obtaining an area difference between NMR T2 spectrums of alternate displacement of shale oil by carbon dioxide and nitrogen for two adjacent times;

(6B) based on the area difference obtained by the step (6A), obtaining an oil displacement efficiency of alternate displacement of shale oil by carbon dioxide and nitrogen for one of the two adjacent times; and (6C) based on the oil displacement efficiency obtained by the step (6B), fitting a relational expression between the oil displacement efficiency and an alternate displacement time of alternate displacement of shale oil by carbon dioxide and nitrogen for multiple times with polynomials, thereby obtaining the expression of oil displacement efficiency change of alternate displacement of shale oil by carbon dioxide and nitrogen for multiple times.

In the present invention, the carbon dioxide and nitrogen are alternately displaced for multiple times to achieve oil displacement, and at the same time, the porosity of the shale core changes with the displacement and the crude oil is continuously displaced, the oil displacement efficiency of alternate displacement of shale oil by carbon dioxide and nitrogen will also change accordingly. The method provided by the present invention comprises measuring the NMR T2 spectrum after each displacement to obtain the efficiency of alternate displacement of shale oil by carbon dioxide and nitrogen for every time through nuclear magnetic resonance, obtaining the relational expression between the oil displacement efficiency and alternate displacement times through fitting, and obtaining a variation trend between the oil displacement efficiency and alternate displacement times, which is able to be used to design the alternate displacement times during the mining process, thus reducing the consumption of carbon dioxide and nitrogen, and improving the economic efficiency.

Preferably, in the step (6), the change rate of porosity is a ratio of a difference between the initial porosity $p_0$ and the porosity p, and the initial porosity $p_0$, which is expressed by a formula of $P_{change\ rate}=(p_0-p)/p_0\times100\%$.

Preferably, in the step (7), the injection volume adjustment expression of alternate displacement of shale oil by carbon dioxide and nitrogen is obtained by a method comprising:

(7A) obtaining a relational expression between the change rate of porosity and the alternate displacement time of alternate displacement of shale oil by carbon dioxide and nitrogen for multiple times by substituting the change rate of porosity into the expression of oil displacement efficiency change of alternate displacement of shale oil by carbon dioxide and nitrogen for multiple times;

(7B) building calculation formulas between an injection volume of alternate displacement of shale oil by carbon dioxide and nitrogen for every time and a porosity of the shale core at this time; and (7C) substituting the calculation formulas obtained by the step (7B) into the relational expression obtained by the step (7A), thereby obtaining the injection volume adjustment expression of alternate displacement of shale oil by carbon dioxide and nitrogen.

Preferably, in the step (7B), the calculation formulas are $V_{total}=V_{mCO2}+V_{mN2}$, $V_{mCO2}=p_m \times V_{shale\ core} \times 0.3$, and $V_{mN2}=p_m \times V_{shale\ core} \times 0.2$, wherein $V_{total}$ is a total injection volume of alternate displacement of shale oil by carbon dioxide and nitrogen for every time, m is the $m^{th}$ alternate displacement time and meets a condition of $1 \le m \le N$, $V_{mCO2}$ is an injection volume of carbon dioxide of alternate displacement of shale oil by carbon dioxide and nitrogen for the $m^{th}$ time, $V_{mN2}$ is an injection volume of nitrogen of alternate displacement of shale oil by carbon dioxide and nitrogen for the $m^{th}$ time, $p_m$ is a porosity of the shale core of alternate displacement of shale oil by carbon dioxide and nitrogen for the $m^{th}$ time, $V_{shale\ core}$ is a volume of the shale core.

Preferably, in the step (3), a volume of the injected carbon dioxide gases is 0.3 times a void volume of the shale core, a volume of the injected nitrogen gases is 0.2 times the void volume of the shale core, an injection pressure of carbon dioxide and nitrogen is in a range of 20 to 30 MPa, and an injection temperature of carbon dioxide and nitrogen is in a range of 90 to 108° C.

At present, since the research on the method of displacement of shale oil is mainly focused on the displacement method, the research on the influence of the injection volume of carbon dioxide of alternate displacement of shale oil by carbon dioxide and nitrogen on the displacement effect is blank. The process of displacement of shale oil by gas phase for multiple times has a greater impact on the porosity of the shale layer, and then affects the displacement effect. Therefore, the inventor of the present invention proposes a simulation analysis method for an injection volume of alternate displacement of shale oil by carbon dioxide and nitrogen. According to the present invention, in the core displacement simulation experiment, the NMR T2 spectrums are used to obtain changes in oil displacement efficiency of alternate displacement of shale oil by carbon dioxide and nitrogen for multiple times at a set temperature and a set pressure, and according to the change of porosity, the injection volume of carbon dioxide and nitrogen, of alternate displacement of shale oil by carbon dioxide and nitrogen for a single time, is adjusted, thus maximizing the oil displacement efficiency and reducing the injection volume of carbon dioxide, which provides reference data and opinions for the design of shale oil production methods.

The preferred embodiments of the present invention are described in detail above. However, the present invention is not limited to the specific details in the above-mentioned embodiments. The above are only the preferred embodiments of the present invention and are not intended to limit the present invention. Any modification, equivalent replacement and improvement made within the spirit and principle of the present invention shall be included in the protective scope of the present invention.

What is claimed is:

1. A simulation analysis device for an injection volume of alternate displacement of shale oil by carbon dioxide and nitrogen, the simulation analysis device comprising a core package apparatus, a nuclear magnetic resonance apparatus, a control apparatus, a confining pressure apparatus, a gas supply pipeline, a gas discharging pipeline, a nitrogen cylinder, a carbon dioxide cylinder, a helium cylinder and a vacuum pump, wherein:

the core package apparatus comprises an elastic rubber tube, a first head and a second head both of which are respectively located at two ends of the elastic rubber tube; the first head has a gas inlet which is communicated with the gas supply pipeline; the second head has a gas pumping port which is communicated with the vacuum pump, and an oil outlet which is communicated with the gas discharging pipeline;

the nitrogen cylinder, the carbon dioxide cylinder and the helium cylinder are communicated with the gas inlet of the core package apparatus through a first sub-pipeline, a second sub-pipeline and a first branch pipeline of the gas supply pipeline, respectively; a nitrogen control valve, a carbon dioxide control valve and a helium control valve are provided on the first sub-pipeline, the second sub-pipeline and the first branch pipeline of the gas supply pipeline for controlling opening and closing of the nitrogen cylinder, the carbon dioxide cylinder and the helium cylinder, respectively;

a pressure monitoring apparatus and a temperature monitoring apparatus are provided on the confining pressure apparatus; the confining pressure apparatus comprises an annular confining pressure housing located at an outer side of the core package apparatus, wherein the annular confining pressure housing and an outer side wall of the core package apparatus form a confining pressure chamber, the core package apparatus is communicated with the confining pressure chamber through the gas inlet, the gas pumping port and the oil outlet;

a flow monitoring apparatus and another pressure monitoring apparatus are installed at each of the gas inlet, the gas pumping port and the oil outlet of the core package apparatus;

the nuclear magnetic resonance apparatus is configured to measure and obtain NMR spectrums of a shale core;

the control apparatus comprises the nitrogen control valve, the carbon dioxide control valve, the helium control valve, multiple flow monitoring apparatuses, multiple pressure monitoring apparatuses and multiple temperature monitoring apparatuses for controlling corresponding elements, respectively.

2. The simulation analysis device according to claim 1, further comprising a preheating and pressure regulating chamber for preheating and regulating a pressure of nitrogen gases and carbon dioxide gases, wherein:

the gas supply pipeline comprises a main pipeline, the first branch pipeline, a second branch pipeline, the first sub-pipeline and the second sub-pipeline, wherein one end of the main pipeline is connected with the gas inlet of the core package apparatus, another end of the main pipeline is connected with the first branch pipeline and the second branch pipeline, respectively;

one end of the first branch pipeline away from the main pipeline is connected with the helium cylinder, one end of the second branch pipeline away from the main pipeline is connected with a gas outlet of the preheating and pressure regulating chamber;

one end of the first sub-pipeline is connected with the nitrogen cylinder, another end of the first-pipeline is connected with the preheating and pressure regulating chamber;

one end of the second sub-pipeline is connected with the carbon dioxide cylinder, another end of the second sub-pipeline is connected with the preheating and pressure regulating chamber.

* * * * *